United States Patent [19]

Borch et al.

[11] Patent Number: 5,403,932

[45] Date of Patent: Apr. 4, 1995

[54] PHOSPHORAMIDATES USEFUL AS ANTITUMOR AGENTS

[75] Inventors: Richard F. Borch, Pittsford; Gregory W. Canute, Tully; Ronald R. Valente, Rochester, all of N.Y.

[73] Assignee: Research Corporation Technologies, Inc., Tucson, Ariz.

[21] Appl. No.: 260,040

[22] Filed: Jun. 15, 1994

Related U.S. Application Data

[63] Continuation of Ser. No. 741,930, Aug. 8, 1991, abandoned, which is a continuation-in-part of Ser. No. 198,408, May 25, 1988, abandoned.

[51] Int. Cl.$^6$ .................. C07F 9/6553; C07F 9/60; C07F 9/58; C07F 9/24
[52] U.S. Cl. .................. 546/22; 544/124; 544/128; 544/146; 544/157; 546/23; 548/119; 558/169; 558/179; 558/191; 549/6
[58] Field of Search .................. 546/22, 23; 558/169, 558/179, 191; 549/6

[56] References Cited

U.S. PATENT DOCUMENTS 3,035,080  5/1962  Arnold et al.
4,826,830  5/1989  Han et al. .................. 514/118

OTHER PUBLICATIONS

Carter, S. K. et al. *Chemotherapy of Cancer*; Second Edition; John Wiley and Sons: New York, 1981; Appendix C.
Chemical Abstracts 1990, 112(21), 198797n; PCT Int. Appl. WO 89-11,484, publ. Nov. 30, 1989.
Ludeman, et al., *Drugs Expt. Clin. Res. XII*, 527–532 (1986).
Ludeman, et al., *J. Med. Chem.*, 29, 716–727 (1986).
Foster, et al., *J. Med. Chem.*, 24, 1399–1403 (1981).
Takamizawa, et al., *Journal of Medicinal Chemistry*, 21, 208–214 (1978).
Friedman, et al., *Cancer Treatment Reports*, 60, 337–346 (1976).

*Primary Examiner*—Mary C. Lee
*Assistant Examiner*—Michael G. Ambrose
*Attorney, Agent, or Firm*—Schwegman, Lundberg & Woessner

[57] ABSTRACT

Compounds of the formula:

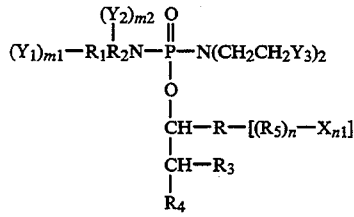

which is further defined herein, possess anti-tumor activity.

9 Claims, No Drawings

PHOSPHORAMIDATES USEFUL AS ANTITUMOR AGENTS

This invention was made with Government support under RO1-CA-34620 awarded by National Institutes of Health. The Government has certain rights in the invention.

CROSS-REFERENCE TO RELATED APPLICATION

This is a continuation of application Ser. No. 07/741,930, filed Aug. 8 1991, now abandoned, which is a continuation-in-part of application Ser. No. 198,408, filed May 25, 1988, now abandoned.

This invention relates to novel phosphoramidates which have useful pharmaceutical properties and are useful as anti-tumor agents.

BACKGROUND OF THE INVENTION

Cyclophosphamide (also known as cytoxan) is one of the most widely used anti-cancer drugs in the world. It is generally administered in combination with a number of other drugs to treat a wide variety of hematologic and solid tumors. However, there are several features of the drug that limit its clinical utility. First, the drug requires cytotoxic activation in the liver to produce metabolites that are toxic to cancer cells. Second, the drug is specifically toxic to the urinary bladder and also displays bone marrow toxicity typical of the alkylating agent class of anti-cancer drugs. Third, cyclophosphamide is a potent suppressor of the immune system at the doses used to treat cancer, thus decreasing the infection-fighting ability of patients already debilitated by their disease. Finally repeated use of cyclophosphamide frequently results in the development of resistance to the drug in a patient's cancer cells, thus rendering the drug ineffective.

The present phosphoramidate compounds circumvent one or more of these problems, because they possess several new, surprising, and highly beneficial properties. First, the present compounds are more cytotoxic under oxygen-deficient conditions than under normal aerobic conditions. Therefore, unlike cyclophosphamide which is cytotoxically activated in the liver, the present compounds become selectively cytotoxic in hypoxic cells. Hence, oxygen-deficient tumor cells are selectively destroyed by concentrations of these compounds which do not affect non-cancerous cells. Second, these compounds are not toxic to the urinary bladder. Third, the compounds of the present invention are effective in treating tumors in animals that have developed resistance to cyclophosphamide.

Therefore, the present compounds represent a substantial improvement over known antitumor agents.

BRIEF DESCRIPTION OF THE PRESENT INVENTION

The present invention relates to new chemical phosphoramidate compounds possessing anti-tumor activity. The subject compounds can liberate cytotoxic metabolites such as phosphoramide mustard or its analogs when exposed to the reducing environment of oxygen-deficient (i.e., hypoxic) cells. Hence, only hypoxic cells are killed by the subject compounds at the concentrations specified by this invention. The compounds of the present invention have the formula:

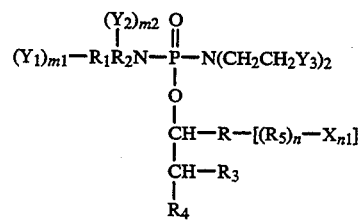

wherein $R_1$ and $R_2$ may be the same or different and are selected from the group consisting of hydrogen, or a lower alkylene which is substituted with $Y_1$ and $Y_2$ on a non-α-carbon of $R_1$ and $R_2$ respectively;

or $R_1$ and $R_2$ taken together with the nitrogen to which they are attached, form a morpholino ring;

$Y_1$, $Y_2$ and $Y_3$ are independently hydrogen, halogen, a lower alkyl sulfonic ester, an arylsulfonic ester, fluoralkylsulfonate, a lower alkyl sulfinic ester, an aryl sulfinic ester or a leaving group;

R is a nitro-substituted aryl or a nitro-substituted nitrogen, sulfur or oxygen containing heterocyclic ring;

$R_5$ is lower alkylene, lower alkenylene, lower alkynylene, arylene, or aryl lower alkylene;

X is hydrogen, halogen, hydroxy, lower alkoxy, carbamoyl, formyl, carboxy, lower carbalkoxy, lower alkylamino, lower alkylaminoalkylene or an electron withdrawing group, and when n is 0, X can be directly attached to R;

$m_1$ and $m_2$ are independently 0 to 1, with the proviso that when $m_1$ is 0, $R_1$ is hydrogen and when $m_2$ is 0, $R_2$ is hydrogen;

n is 0 to 4;

$n_1$ is 1 to 4;

$R_3$ and $R_4$ are independently hydrogen, hydroxy, lower alkoxy, lower carbalkoxy, lower dialkylamino-lower alkyleneoxycarbonyl, an electron withdrawing group, or a lower alkyl containing up to 6 carbon atoms in the main chain and up to a total of 10 carbon atoms, which may have an electron withdrawing group substituent;

or a pharmaceutically acceptable salt thereof.

DETAILED DESCRIPTION OF THE INVENTION

As used herein, a lower alkylene, singly or in combination with other groups, contains up to six carbon atoms in the main chain and a total of 10 carbon atoms if the alkylene is branched. Lower alkylene groups include methylene, ethylene, propylene, isopropylene, butylene, t-butylene, sec-butylene, isobutylene, amylene, isoamylene, pentylene, isopentylene, hexylene and the like. The preferred lower alkylene groups contain one to three carbon atoms.

As used herein, a lower alkyl, singly or in combination with other groups, contains up to six carbon atoms in the main chain and a total of 10 carbon atoms if the alkyl is branched. Lower alkyl groups include methyl, ethyl, propyl, isopropyl, butyl, t-butyl, sec-butyl, isobutyl, amyl, isoamyl, pentyl, isopentyl, hexyl and the like. Methyl and ethyl groups may be abbreviated herein as Me and Et, respectively. The preferred lower alky groups contain one to three carbon atoms.

As used herein, lower alkenylene is an unsaturated hydrocarbon containing two to six carbon atoms and at least one double bond but not more than three double bonds. Lower alkenylenes may be in normal or branched configuration and include such groups as ethenylene, 1-propenylene, 2-propenylene, 1-butenylene, 2-butenylene, 3-butenylene, isobutenylene and the like.

The term lower alkynylene as used herein refers to an unsaturated hydrocarbon containing two to six carbon atoms and one to three triple bonds. Alkynylenes may be in a normal or branched configuration. Examples of alkynylenes include ethynylene, butynylene, pentynylene, hexynylene, and the like.

Aryl or arylene groups are aromatic rings containing from 6 to 14 ring carbon atoms and a total of 18 carbons when aryl or arylene groups have lower alkyl substituents. Aryl or arylene groups with lower alkyl substituents are also referred to herein as lower alkyl aryl or lower alkyl arylene. Aryl groups include such groups as phenyl, $\alpha$-naphthyl, $\beta$-naphthyl and the like. An aryl or arylene group is preferably phenyl. An aryl lower alkylene is an aryl, as defined herein, attached to the remainder of the molecule via a lower alkylene. Examples of aryl lower alkylene and lower alkyl arylene groups include benzyl, tolyl, xylyl, phenethyl, methylnaphthyl, naphthalmethylene, and the like.

As employed herein, "nitrogen, sulfur or oxygen heterocyclic ring" means heterocyclic rings having at least one sulfur, nitrogen or oxygen ring atom but which can have several of such atoms. It is preferred that a heterocyclic ring have only nitrogen, sulfur or oxygen heteroatoms. Heterocyclic rings may be monocyclic, bicyclic or polycyclic. If a heterocyclic ring is bicyclic or polycyclic, the rings are fused. The heterocyclic group may contain up to 4 ring heteroatoms and up to a total of 18 ring atoms. The ring heteroatoms may be the same or different. It is preferred that the heterocylic ring contain 1 or 2 ring heteroatoms, most preferred is 1 ring heteroatom. Moreover, it is preferred that the heterocyclic ring contain from 5 to 14 ring atoms and from 4 to 13 ring carbon atoms. Hetrocyclic rings can also have a mixture of 1-2 different nitrogen, sulfur or oxygen heteroatoms, e.g. morpholine with one oxygen and one nitrogen. Nitrogen, sulfur or oxygen heterocylic rings also include saturated and unsaturated heterocyclic, as well as heteroaromatic and benzoheterocyclics rings. Representative saturated heterocyclic rings include tetrahydrofuran, indoline, pyrazolidine, imidazoline, imadazolidine, pyrrolidine, epoxy, aziridine, azetidine, pyrroline, piperidine, piperazine and morpholine.

Heteroaromatic rings are aromatic rings containing up to 4 ring heteroatoms and up to 18 ring atoms. Representative heteroaromatic rings include thiophene, benzothiophene, naphthothiophene, trianthrene, furan, benzofuran, isobenzofuran, pyran, chromene, xanthene, phenoxathiin, pyrrole, imidazole, pyrazole, pyridine, pyrazine, triazole, tetrazole, pyrazine, triazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, isothiazole, phenothiazine, oxazole, isoxazole, furazan, phenoxazine and the like. Preferred heteroaromatic groups include imidazole, pyridine, pyrimidine, quinoline, isoquinoline, thiophene and the like.

It is preferred that the heterocyclic ring be either monocyclic or bicyclic heteroaromatic with 1 or 2 ring heteroatoms and 5 to 10 ring atoms. Especially preferred heterocyclic rings have 4 to 9 carbon atoms.

Halogen groups include fluorine, chlorine, bromine and iodine. Bromine and chlorine are preferred halo groups.

A lower alkoxy substituent is a lower alkyl covalently attached via an oxygen atom. A lower alkanoyl substituent is a lower alkyl containing a carbonyl group.

A lower thioalkyl is a lower alkyl with an —SH substituent.

A carboxy is a —COOH group.

An aryloxy substituent is an aryl group attached via the oxygen atom.

A lower carbalkoxy group is a lower alkoxy attached to an acyl (i.e. —CO—).

A carbamoyl group is an acyl (—CO—) attached to an alkylamino group, e.g. —CO—$NR_6R_7$, wherein $R_6$ and $R_7$ are independently hydrogen or lower alkyl.

A lower alkylamino is a nitrogen atom with one, two or three lower alkyl substituents which is attached via the nitrogen atom to the remainder of the molecule. As used herein, alkylamino includes mono-lower alkylamino, di-lower alkylamino and tri-lower alkylamino.

A lower alkylaminoalkylene is an alkylene with a lower alkylamino substituent attached to the remainder of the molecule via a carbon on the alkylene.

A sulfonic ester is a —$OSO_2$— group; and a sulfinic ester is an —SO—O— group.

A lower alkyl sulfonic ester is a —$OSO_2$-lower alkyl and a lower alkyl sulfinic ester is a —SO—O-lower alkyl.

A arysulfonic ester is a —$OSO_2$-aryl and an arylsulfinic ester is a —SO—O-aryl wherein the aryl may be substituted with 1-3 lower alkyl groups, 1-2 halogens or 1-2 nitro group.

A lower dialkylamino-lower alkylene-oxy-carbonyl is a lower alkylene with a —COO-lower alkyl substituent wherein the lower alkyl has an alkylamino substituent. Preferred lower dialkylamino lower alkylene oxycarbonyl groups have a formula —$(CH_2)_{q1}$—CO—O—$(CH_2)_{q2}$—$N[(CH_2)_{q3}CH_3]_2$ wherein q1, q2 and q3 are independently 0–3. More preferred values for q1 are 1 to 2. Preferred values for q2 are 1 to 3 and it is preferred that q3 be 0 to 1. Especially preferred lower dialkylamino-lower alkyleneoxycarbonyls have the formula —$CH_2$—CO—O—$CH_2$—$CH_2$—$N(CH_3)_2$.

Carboxy lower alkylene groups are lower alkylene groups with a carboxy substituent.

Tri-halo methyl groups are methyl groups with three halogen substituents.

Lower dialkyl-mercaptans are lower alkylene groups with an —S-lower alkyl substituent.

Lower fluoroalkylsulfonates are —$OSO_2$—$(CH_2)_{v1}$—$CF_3$ or —$OSO_2$—$CF_2$—$CF_3$ groups wherein v1 is 0 to 6. Preferred values for v1 are 0 or 1.

An $\alpha$-carbon, with respect to the alkylene chain of $R_1$ or $R_2$, is the carbon atom on each of those chains which is adjacent to the nitrogen of the phophoramide. Any substitutent on $R_1$ or $R_2$ is bonded to a carbon other than the $\alpha$-carbon, i.e. a non-$\alpha$-carbon. It is preferred that $R_1$ and $R_2$ substitutents be on the $\beta$ carbon.

As is generally known in the art, and for the purposes of the present invention, "a leaving group" is defined as a group which is readily broken away from its union with a carbon atom by nucleophilic attack on that carbon atom. For example, a leaving group often can join with an active hydrogen atom and thereby break away from a carbon. Leaving groups are generally electron withdrawing groups either because of their electronegativity or because they have an inductive effect.

Without wishing to be so bound, the present compounds are thought to act as alkylating agents of DNA, with the $Y_1$, $Y_2$ or $Y_3$ groups acting as leaving groups replaced by DNA. Leaving groups contemplated by the present invention include halogen, hydroxy, lower alkoxy, carboxy lower alkylene, lower carbalkoxy, trifluoromethylene, lower dialkyl-mercaptan, cyano, lower alkyl fluorosulfonates, aryloxy, sulfonic or sulfinic esters, including lower alkyl sulfonates like methyl sulfonate (i.e. mesylate) or ethyl sulfonate and ammonioalkylsulfonate (i.e. betylates), as well as arylsulfonic esters, such as tolylsulfonates (i.e. tosylates), bromophenylsulfonates (i.e. brosylates), nitrophenylsulfonates (i.e. nosylates) and the like. Preferred lower fluoroalkylsulfonates include trifluoromethylsulfonates (i.e. lower alkyl-$OSO_2CF_3$ or triflates) nonafluorobutylsulfonates (i.e. lower alkyl-$OSO_2$—$C_4F_9$) or nonaflates and 2,2,2-trifluoroethylsulfonates (i.e. lower alkyl-$OSO_2$—$CH_2$—$CH_2CF_3$ or tresylates). Preferred leaving groups are halogen, carboxy lower alkylene, lower alkyl sulfonic ester or arylsulfonic ester. More preferred $Y_1$, $Y_2$ and $Y_3$ leaving groups are Br, Cl, carboxy lower alkoxy, mesylates, betylates, tosylates, brosylates, nosylate, triflate, nonaflate or tresylate.

As used herein an electron withdrawing group is a group that will draw electrons to itself more than a hydrogen atom would if it occupied the same position in the molecule (Jerry March, 1977 "Advanced Organic Chemistry," 2nd ed., McGraw Hill, New York, p. 21). Electron withdrawing groups include lower alkanoyl, lower alkoxy, formyl, lower alkenyl, lower alkynyl, aryl, lower alkyl arylene, hydroxy, thio, lower thioalkyl, carboxy, lower carbalkoxy, aryloxy, halogen, nitro, cyano, quarternary salts of lower mono-, di- and tri-alkylamino, and the like.

The preferred $R_1$ and $R_2$ groups are hydrogen or alkylene containing 1 to 3 carbon atoms on the main chain. Preferred $R_1$ and $R_2$ groups have 2 carbons. Both $R_1$ and $R_2$ may be monosubstituted with $Y_1$ and $Y_2$, respectively, at any position except at the s-position (i.e., the carbon adjacent to the nitrogen in the phosphoramide). It is preferred that $R_1$ and $R_2$ groups be substituted on the beta carbon i.e., the second carbon on the alkyl chain from the nitrogen. Preferred substituents are halogens and lower alkyl sulfonic esters or arylsulfonic esters. The preferred $R_1$ and $R_2$ groups are hydrogen and ethylene independently substituted with preferred leaving groups: Br, Cl, lower fluoroalkylsulfonate, carboxy lower alkyl, lower alkyl sulfonic ester or arylsulfonic ester, mesylate, tosylate, brosylate, nosylate, trillate, nonaflate, or tresylate. It is also preferred that $R_1$ be the same as $R_2$.

Moreover, as defined hereinabove, $R_1$ and $R_2$ taken together with the nitrogen to which they are attached can form a morpholino ring. A morpholino ring is also preferred for $R_1$ and $R_2$.

m1 and m2 can be 0 to 1, i.e. $R_1$ and $R_2$ can have 0 to 1 $Y_1$ and $Y_2$ substituents, respectively. Moreover, when m1 is 0 then $Y_1$ is not present and $R_1$ is hydrogen and when m2 is 0 then $Y_2$ is not present and $R_2$ is hydrogen.

The $R_3$ and $R_4$ substituents are independently hydrogen, hydroxy, lower alkoxy, lower carbalkoxy, lower dialkylamino-lower alkyeneoxycarbonyl, an electron withdrawing group, or an alkylene group, with the alkylene group having zero to one alkyl or electron-withdrawing group substituents. The alkylene group can have up to 6 carbons in the main chain and up to a total of 10 carbon atoms if in branched conformation. The function of the electron withdrawing group is to make the hydrogen on $R_4CH$—$R_3$ weakly acidic, that is, removable by base. It is preferred that the electron withdrawing group, when present on $R_3$ or $R_4$, is on the alpha ($\alpha$) carbon, that is, on the first carbon atom of the $R_3$ or $R_4$ chain. The preferred $R_3$ and $R_4$ groups are hydrogen, lower alkyl, lower alkoxy, lower carbalkoxy, especially carbomethoxy (—$COOCH_3$) or carboethoxy (—$COOCH_2CH_3$), and lower dialkylamino lower alkyleneoxycarbonyl, especially —$CH_2COOCH_2CH_2N(CH_3)_2$.

The R groups as defined hereinabove are nitro substituted aryl or heterocyclic rings. The nitro group may be substituted on any position of an aryl or heterocyclic ring but is preferably not on a ring heteroatom. Preferred nitro substituted heterocyclic R groups have a 5 or 6 membered heteroaromatic ring which may or may not be fused to an aromatic ring. Preferred R groups include nitrothiophenes e.g. 2-nitrothiophene or 3-nitrothiophene, nitrophenyls e.g. 2-nitrophenyl or 4-nitrophenyl, nitropyridines, nitroquinolines, nitroisoquinolines, nitropyrroles, nitrofurans, and nitroimidazoles.

The preferred nitropyridine R groups are attached to the rest of the phosphoramide by a ring carbon adjacent to the nitrogen heteroatom of the pyridine. While the nitro group may be on any unsubstituted position on the pyridine ring, more preferred positions are the beta or gamma positions, relative to the nitrogen heteroatom. Preferred nitropyridine R—$(R_5)_n$—$X_{n1}$ groups are:

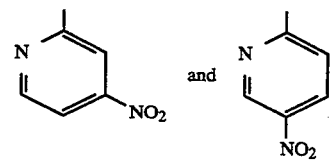

As defined herein quinolines and isoquinolines are numbered as depicted below:

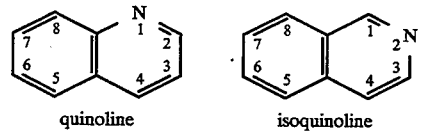

quinoline     isoquinoline

The preferred nitroquinolines have the nitro group on the 3 or 4 position relative to the nitrogen heteroatom. Preferred compounds also have the nitro on the 3 or 4 position of the quinoline with the $R_5$—X group on a non-nitrogen ring atom which is not immediately adjacent to the nitro group. More preferred nitroquinolines have an $R_5$—$X_{n1}$ on quinoline positions 5, 6, 7 or 8, the nitro in position 3, and the linkage between the rest of the phosphoramide molecule and the quinoline at positions 5, 6, 7 or 8. The most preferred linkage position is 8. The most preferred nitroquinolines are of the formulae:

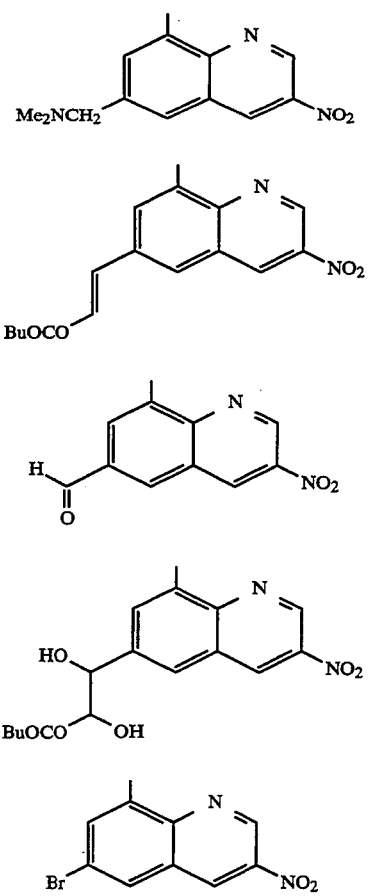

i.e. wherein the nitro is on the 3 position and $R_5X_{n1}$ is —CH$_2$N(CH$_3$)$_2$, formyl, Br, —CH(OH)—CH(OH)—COOC$_4$H$_9$, or —CH=CH—COOC$_4$H$_9$. Especially preferred nitroquinolines have the nitro group at the 3 position with —CH$_2$N(CH$_3$)$_2$ for $R_5X_{n1}$.

Preferred nitroisoquinolines have a nitro group at position 4 and linkage to the rest of the phophoramide at position 1.

The preferred nitroimidazoles are lower alkyl substituted nitroimidazoles wherein lower alkyl contains from 1 to 6 carbon atoms. Especially preferred lower alkyl imidazoles are N-lower alkyl imidazoles having the formula:

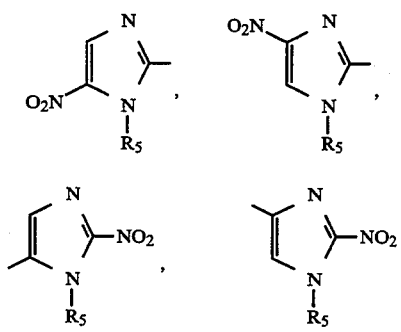

wherein $R_5$ is lower alkyl and X is hydrogen.

Especially preferred R groups are 2-nitrothiophene, 2-nitrophenyl, 4-nitrophenyl, 3-nitro-quinoline and the foregoing N-lower alkyl imidazoles.

$R_5$ groups can be hydrogen, lower alkylene, lower alkenylene, lower alkynylene or arylene. Preferred $R_5$ groups are hydrogen, or lower alkylene or lower alkenylene having 1 to 3 carbon atoms, i.e. methylene, ethylene, propylene, ethylene, propenylene or isopropenylene. Especially preferred $R_5$ groups are hydrogen, methylene, ethylene or ethenylene.

X substituents are present on $R_5$, or when n is 0, $X_{n1}$ can be directly attached to R. Preferred X substituents on $R_5$ or R groups are hydrogen, hydroxy, formyl, lower carbalkoxy, lower alkylamino, lower alkylaminoalkylene and related groups.

$R_5$—X groups on heteroaromatic rings are preferably substituted on a carbon ring atom which is not immediately adjacent to the nitro group. Preferred $R_5$—$X_{n1}$ groups include hydrogen, lower alkyl, lower hydroxyalkyl, lower dihydroxyalkyl, lower alkenyl, formyl, carbalkoxy lower alkenyl, lower carbalkoxy-dihydroxy-lower alkylene, or di-lower alkylaminoalkylenes e.g. —CH$_3$, —CH$_3$—CH(OH)—CH(OH)—CO—OC$_4$H$_9$, —CH=CH—CO—OC$_4$H$_9$, —CHO, and —CH$_2$N(CH$_3$)$_2$, and the like. Especially preferred $R_5$—$X_{n1}$ groups are di-lower alkyl aminoalkylene.

n can be 0 to 4, and $n_1$ can be 1 to 4 i.e. zero to four $R_5$ substituents can be present on the R aryl or hetrocyclic ring and each $R_5$ can have one to four X substituents. Preferred values of n are 0 to 2. The most preferred values of n are 0 to 1. Preferred values of $n_1$ are 1 to 3.

Without wishing to be bound, it is thought that the function of an $(R_5)_n$—$X_{n1}$ substituent is twofold. First, $(R_5)_n$—$X_{n1}$ is present to enhance the solubility of the present phosphoramide compounds. Hence, preferred $R_5$—$X_{n1}$ groups have a charge at physiological pH (i.e. at about pH 7.4). Moreover, preferred charged $(R_5)_n$—$X_{n1}$ groups are the quarternized substituents of $R_5$—$X_{n1}$ described hereinabove. The second function of an $(R_5)_n$—$X_{n1}$ is to make the redox potential of the R group less negative. To achieve this $(R_5)_n$—$X_{n1}$ substituents which are electron withdrawing groups are preferred. Preferred R—$(R_5)_n$—$X_{n1}$ groups have a first one-electron redox potential in the range of $-200$ mV to $-500$ mV.

It is also preferred that when n is 0, X is hydrogen, m1 and m2 are 0, $R_1$ and $R_2$ are hydrogen and $Y_3$ is Cl, i.e. compounds of the formula:

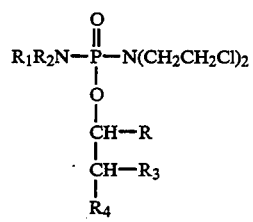

The compounds of the present invention can be prepared by art recognized techniques. Exemplary procedures are outlined below wherein R, $R_1$, $R_2$, $R_3$, $R_4$, $R_5$, X, $Y_3$, n and $n_1$ are defined as hereinabove:

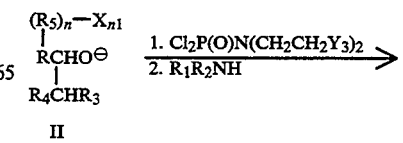

II

-continued

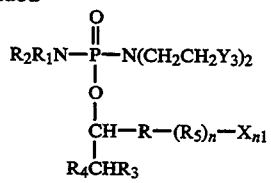

I

An alkoxide of Formula II is reacted with, for example, N,N-bis(2-haloethyl)phosphoramidic dichloride, followed by the addition of an amine $R_1R_2NH$ to form the compound of Formula I. It is preferable that the reaction take place in an inert organic solvent such as methylene chloride, dioxane, tetrahydrofuran, hexane and the like. The reaction can take place at temperatures ranging from the melting point of the solvent to reflux temperatures, but it is preferred that the reaction take place from about $-60°$ C. to room temperature.

The alkoxide of Formula II can be prepared by reacting the corresponding alcohol

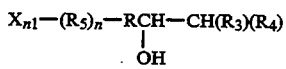

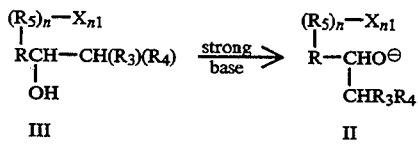

with a strong base, such as alkali metal, an hydroxide or amide of an alkali metal, or a strong metal organic base, e.g., alkoxide, metal alkylamides, metal alkylsilylamides, e.g. lithium bis-trimethyl-silylamide and the like or an organo-metallic compound, such as metallic alkyls, such as n-butyl lithium and the like, in accordance with procedures known to one skilled in the art.

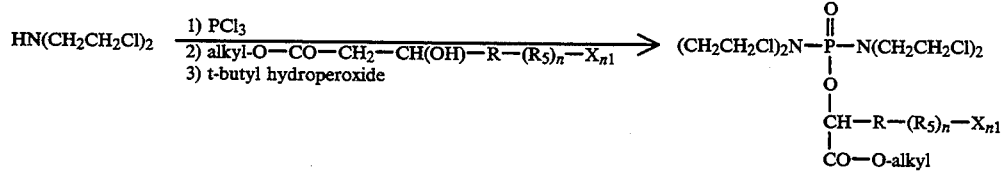

An alternative procedure for forming the alkoxide of Formula II is to couple an aldehyde having the formula $X_{n1}-(R_5)_n-RCHO$ with an organometallic reagent containing a $(CHR_3R_4)$ moiety. For example the organometallic may be an alkali metal, e.g., $Li(CHR_3R_4)$ or a Grignard reagent such as $CHR_3R_4Mg-Z$, wherein Z is halo and the like. The alkali organometallic can be generated by procedures known to one skilled in the art. For example, the Grignard can formed by reacting Mg with the halide of Formula $Z-CHR_3R_4$ wherein Z is halo, under Grignard forming conditions. Alternatively, when the electron withdrawing group is on the alpha carbon of $R_3$ or $R_4$, $CHR_3R_4$ can be metallated by active metals, such as alkali metals to form the $MCHR_3R_4$, wherein M is the active metal using metallation reagents, such as lithium bis(trimethylsilyl)amide and the like, under metallation conditions (Jerry March, "Advanced Organic Chemisrty," 2nd ed, McGraw Hill, NY, N.Y. p. 555 1977). For example, methyl acetate can be converted to methyllithioacetate $LiCH_2COOMe$ by treatment with $LiN(SiMe_3)_2$ in tetrahydrofuran at $-78°$ C. Alternatively, chlorotitanium trisopropoxide can be used in place of $LiN(SiMe_3)_2$ when other lower alkyl esters are used. A nitroarylaldehyde can then be added and the mixture can be warmed to about $0°$ C. to form the alcohol product (III).

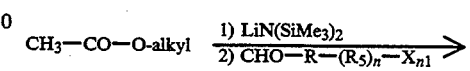

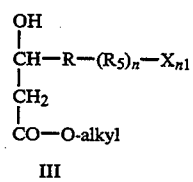

III

If $R_1$ and $R_2$ are 2-haloethyl, then phosphorus trichloride can be reacted with N,N-bis-(2-haloethyl)amine hydrochloride in the presence of an alkylamine base. The alcohol (III) produced from the above reaction can then be added followed by an oxidizing agent such as t-butyl hydroperoxide or iodine to form one species of the final product (I):

The present new compounds which contain basic nitrogen can form salts with acids. All such acid salts are contemplated by the invention but preferred salts are formed with pharmaceutically acceptable acids, such as hydrochloric, sulfuric, nitric, toluenesulfonic, acetic, propionic, tartaric, malic and similar such acids well known in this art. In addition, quaternary salts can be formed using standard techniques of alkylation employing, for example, hydrocarbyl halides or sulfates such as methyl, ethyl, benzyl, propyl or allyl halides or sulfates.

Compounds of the present invention were designated to selectively kill oxygen-deficient (i.e., hypoxic) cells. Hypoxic cells in tumors are generally resistant to radiation and chemotherapy and thus represent a population of cells that are very difficult to eradicate. Most mammaliam cells operate under conditions of oxygen excess and utilize oxidative metabolism. Hypoxic cells, however, represent a reducing environment; a prodrug designed to be activated by the reducing environment inside such cells provides a mechanism to deliver a cytotoxic species specifically to the tumor cell and thus offers a potential therapeutic advantage over known compounds. The compounds of the present invention are prodrugs that will liberate phosphoramide mustard or an analog (cytotoxic metabolites derived from cyclophosphamide) when exposed to the reducing environment of the hypoxic cell. The compounds of the present invention are selectively less cytotoxic under normal aerobic (or oxic) conditions but highly cytotoxic under hypoxic conditions.

The effectiveness of these compounds is believed to result from the reduction of the nitro groups in the hypoxic cells. It is believed that this reduction facilitates expulsion of the cytotoxic phosphoramide mustard moiety. Once released, the phosphoramide mustard becomes an alkylating agent.

The compounds of the present invention can be administered to the host in a variety of forms adapted to the chosen route of administration, i.e., orally, intravenously, intramuscularly or subcutaneous routes.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Compositions or preparations according to the present invention are prepared so that an oral dosage unit form contains an amount ranging from about 100 mg to about 5 g of active compound. Preferred dosage ranges from about 50 to about 1000 mg of active compound. Especially preferred dosage ranges from about 100 mg to about 500 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring may be added. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying techniques which yield a powder of the active ingredient plus any additional desired ingredient from previously sterile-filtered solutions thereof.

The following examples further illustrate the invention.

EXAMPLE 1

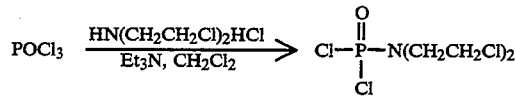

Preparation of Bis-(2-chloroethyl)phosphoramide dichloride

A solution of phosphorus oxychloride (15.33 g, 0.10 mol) in CH$_2$Cl$_2$ (80 ml) was cooled to 0°. Bis-(2-chloroethyl)amine hydrochloride (17.85 g, 0.10 mol) was added directly. Triethylamine (30.66 ml, 0.22 mol) was added dropwise with constant stirring at 0° with a steady flow of nitrogen exiting through an aqueous solution of NaHCO$_3$. The reaction was then warmed to room temperature by allowing the ice bath to melt. After stirring for 34 hours, 10% KH$_2$PO$_4$ in water (60 ml) was added. The solution was extracted with CH$_2$Cl$_2$ (3×30 ml) and the combined organic extracts washed again with 10% aq. KH$_2$PO$_4$ (3×20 ml), and then dried over MgSO$_4$. Removal of solvent under reduced pressure gave a crude solid which was distilled (b.p. 121°–122°, 0.5 mm) to provide pure product (19.3 g, 84%) as a white solid; R$_f$=0.67 (EtOAc:hex 1:2); m.p. 57°–59° C.

$^{31}$P NMR (CHCl$_3$) δ=−7.14 ppm.

IR (nujol) 1290, 1275, 1260, 1220 (P=O), 1195, 1160, 1150, 1110, 1095, 1060, 1030, 1010, 980, 975, 940, 920, 885, 850, 770, 750, 710, 665 cm$^{-1}$.

EXAMPLE 2

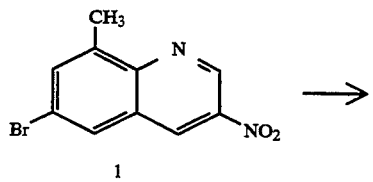

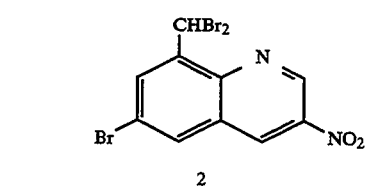

Preparation of 6-Bromo-8-dibromomethyl-3-nitroquinoline(2)

A suspension of 28.56 g (0.107 mol) of 6-bromo-8-methyl-3-nitroquinoline(1) in 330 ml of CH$_3$CCl$_3$ was heated to reflux, cooled slightly, then 52.8 g (0.297 mol) of N-bromosuccinimide and 2.90 g (17.7 mmol) of AIBN were added. The mixture was refluxed for 7½ hr. One additional portion of NBS (10,7 g, 60.1 mol) was added after 3½ hr.; three additional portions (0.30 g, 1.8 mmol; 0.35 g, 2.1 mmol; 0.32 g, 2.0 mmol) of AIBN were added at 2 hr., 3½ hr and 5 hr., respectively. The mixture was cooled to room temp. and some of the CH$_3$CCl$_3$ (230 ml) was removed by rotary evaporation. The remaining slurry was triturated and washed thoroughly with 4:1 (v:v) CH$_3$CN: H$_2$O (4 portions, total of 750 ml), followed by water (2×150 ml), followed by 95% EtOH (150 ml). The product was air dried and recrystallized from 680 ml of CH$_3$CN, (filtered hot to remove traces of an insoluble solid impurity) to give 29.87 g (65.7%) of 6-bromo-8-dibromomethyl-3-nitroquinoline(2) as a tan solid: mp 175°–180° C.; $^1$H NMR δ 8.072(s, 1H, ArCHBr$_2$), 8.211(d, 1H, J=2.1 Hz, Arh), 8.635(d, 1H, J=2.1 Hz, ArH), 8.977 (d, 1H, J=2.6 Hz, ArH), 9.685 (d, 1H, J=2.6 Hz, ArH); IR 1610, 1590, 1535, 1340, 1310 cm$^{-1}$.

EXAMPLE 3

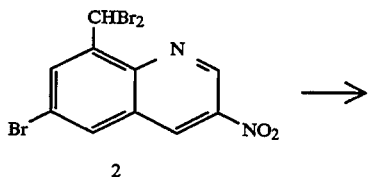

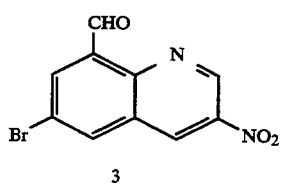

Preparation of 6-Bromo-3-nitroquinoline-8-carboxaldehyde (3)

A solution of 29.87 g (70.3 mmol) of 6-bromo-8-dibromomethyl-3-nitroquinoline(2) 47 ml of N-methylpiperazine and 15 ml of water in 370 ml of CH$_3$CN was refluxed for 20 min., then 300 ml of water and 75 ml of acetic acid were added, and the mixture was cooled in the refrigerator for one day. The mixture was then filtered, and the solid product washed with water (2×60 ml), and EtOH (50 ml) and air dried to give 14.60 g (75%) of crude 6-bromo-3-nitroquinoline-8-carboxaldehyde(3) as a brown solid. This product was used without further purification. The sample for elemental analysis was recrystallized from n-butyronitrile to give tan needles: mp 177°–180° C.; $^1$H NMR δ8.478(d, 1H, J=2.3 Hz, ArH), 8.567(d, 1H, J=2.3 Hz, ArH), 9.062(d, 1H, J=2.6 Hz, ArH), 9.792 (d, 1H, J=2.6 Hz, ArH), 11.348(s, 1H, CHO); IR 1690, 1610, 1560, 1530, 1310 cm$^{-1}$; anal. calcd for C$_{10}$H$_5$N$_2$O$_3$Br: C, H, N.

EXAMPLE 4

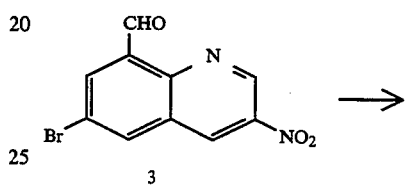

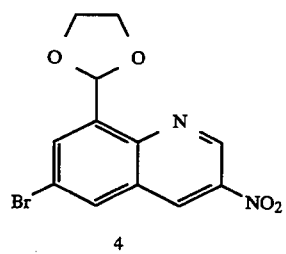

Preparation of 6-Bromo-8(1,3-dioxolan-2-yl)-3-nitroquinoline(4)

A solution of 14.60 g (52.0 mmol) of crude 6bromo-3-nitroquinoline-8-carboxaldehyde and 31 ml of ethylene glycol in 220 ml of n-butyronitrile was heated to distill, and 80 ml of solvent was distilled off over a period of 25 min. The solution was cooled at 4° C. for one day, filtered, and the solid product washed with EtOH (4×20 ml) and air dried to give 14.70 g (87%) of 6-bromo-8-(1,3-dioxolan-2-yl)-3-nitroquinoline(4) as tan crystals: mp 197°–198.5° C.; $^1$H NMR δ4.16–4.27(m, 4H, OCH$_2$CH$_2$O), 6.894(s, 1H, acetal), 8.202(d, 1H, J=2.3 Hz, ArH), 8.273(d, 1H, J=2.3 Hz, ArH), 8.946(d, 1H, J=2.6 Hz, ArH), 9.700 (d, 1H, J=2.6 Hz, ArH); IR 1600, 1530, 1365, 1340, 1310 cm$^{-1}$.

EXAMPLE 5

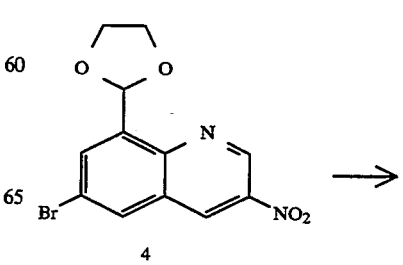

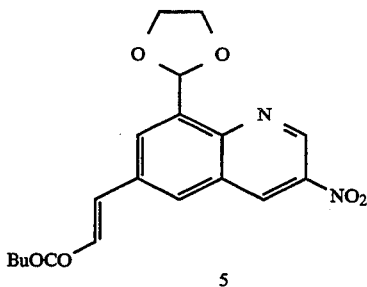

n-Butyl 3-(8-(1,3-dioxolan-2-yl)-3-nitroquinolin-6-yl) propenoate (5)

A suspension of 14.57 g (44.8 mmol) of 6-bromo-8-(1,3-dioxolan-2-yl)-3-nitroquinoline, 0.540 g (2.40 mmol) of Pd(OAc)$_2$, 8.29 g (101 mmol) of NaOAc, and 1.446 g (5.52 mmol) of triphenylphosphine was stirred at room temperature under N$_2$ for 10 min., then 10.4 ml (72.7 mmol) of n-butyl acrylate was added, and the solution was heated at 130°–135° C. for 85 min. with rapid stirring. After cooling, 70 ml of EtOH was added, and the mixture was stirred and triturated for 90 min., then filtered. The solid product was washed with 50 ml of 95% EtOH, then water (3×70 ml), then 95% EtOH again (2×50 ml), air dried, and dissolved in 450 ml of 5:1 CHCl$_3$:EtOAc (v:v) with gentle heating. This solution was filtered through a short column (60 g) of flash silica, eluting with 5:1 CHCl$_3$:EtOAc (v:v). Evaporation of solvents left 11.65 g (70%) of n-butyl 3-(8-(1,3-dioxolan-2-yl)-3-nitroquinolin-6-yl)propenoate (5) as off-white crystals: mp 183°–186° C.; $^1$H NMR δ 0.992 (t, 3H, J=7.3 Hz, methyl), 1.47 (sextet, 2H, J=7.5 Hz, butyl), 1.73 (quintet, 2H, J=7.2 Hz, butyl), 4.20–4.30(m, 6H butyl and OCH$_2$CH$_2$O), 6.698(d, 1H, J=16.0 Hz, alkene), 6.908(s, 1H, acetal), 7.854(d, 1H, J=16.0 Hz, alkene), 8.102(d, 1H, J=1.8 Hz, ArH), 8.414(d, 1H, J=1.8 Hz, ArH, 9.050(d, 1H) J+2.6 Hz, ArH), 9.710 (d, 1H, J+2.6 Hz, ArH): IR 1710, 1640, 1605, 1350, 1330 cm$^{-1}$.

EXAMPLE 6

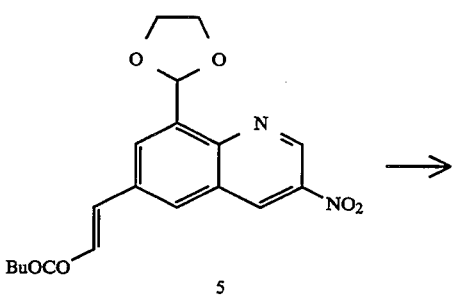

Preparation of n-Butyl 3-(3-nitroquinoline-8-carboxaldehyde-6-yl)-propenoate (6)

A solution of 11.65 g (31.3 mmol) of n-butyl 3-(8-(1,3-dioxlan-2-yl)-3-nitroquinolin-6-yl) propenoate (5) and 23 ml of water in 300 ml of acetic acid was heated to reflux for 1 hr.; 20 ml of water was added to the hot solution, and the mixture was cooled at 4° C. for 2 days. The product was filtered, washed with 2 portions of water and 1 small portion of EtOH, then dried in air to give 9.73 g (95%) of n-butyl 3-(3-nitroquinoline-8-carboxaldehyde-6-yl)-propenoate (6) as light orange-white needles: mp 177°–180° C.; $^1$H NMR δ 0.992(t, 3H, J=7.4 Hz, methyl), 1.47(sextet, 2H J=7.5 Hz, butyl), 1.73(quintet, 2H, J=7 Hz, butyl), 4.273(t, 2H, J=6.6 Hz, butyl), 6.765(d, 1H, J=16.2 Hz, alkene) 8.532(d, 1H, J=1.9 Hz, ArH), 8.698(d, 1H, J=1.9 Hz, ArH), 9.144(d, 1H, J=2.4 Hz, ArH), 9.788(d, 1H, J=2.4 Hz, ArH), 11.400(s, 1H, aldehyde); IR 1705sh, 1695, 1645, 1600, 1575, 1530, 1345, 1330 cm$^{-1}$; anal. calcd for C$_{17}$H$_{16}$N$_2$O$_5$: C, H, N.

EXAMPLE 7

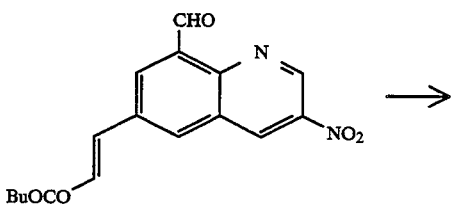

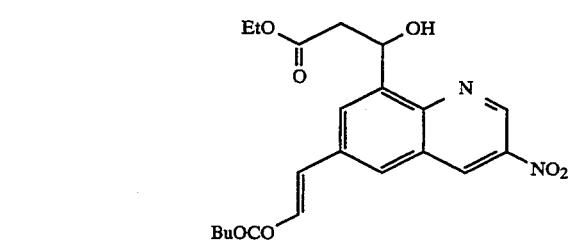

Preparation of n-Butyl 3-(8-[ethyl 3-hydroxypropanoate)-3-yl]-3-nitroquinolin-6-yl) propenoate A mixture of 8.89 g (27.1 mmol) of n-butyl 3-(3-nitroquinoline-8-carboxaldehyde-6-yl)-propenoate (6) and 8.00 g (30.1 mmol) of MgBr$_2$—Et$_2$O was refluxed for 20 min. under N$_2$; 9.30 ml of t-butyl dimethylsilyl ethyl ketene acetal was added via syringe over a period of 160 sec. with rapid stirring. The mixture was refluxed for an additional 80 sec., then 200 ml of 10% aq. acetic acid was immediately added. The heterogeneous mixture was stirred for 5 min., 250 ml of CHCl$_3$ was added and the mixture stirred until all solids had dissolved. After dilution with water (700 ml) the CHCl$_3$ layer was separated, dried (MgSO$_4$), and the solvent evaporated to leave an orange solid. The crude products were subjected to flash chromatography, eluting first with 20:1 CH$_2$Cl$_2$:EtOAc (v:v), followed by 4:1 CH$_2$Cl$_2$:EtOAc (v:v) to give 2.34 g (26%) of recovered starting material, followed by 6.64 g (59%) of n-butyl 3-(8-[(ethyl 3-hydroxypropanoate)-3-yl]-3-nitroquinolin-6-yl) propenate (7) as a pale orange solid, which was pure by $^1$H NMR. A small sample was recrystallized from toluene for elemental analysis; off-white crystals: mp 163°–166° C.; $^1$H NMR δ 0.989(t, 3H, J=7.3 Hz, CH$_2$CH$_2$CH$_2$CH$_3$), 1.265(t, 3H, J=7.1 Hz, OCH$_2$CH$_3$), 1.47(sextet, 2H, J=7.5 Hz, OCH$_2$CH$_2$CH$_2$CH$_3$), 1.83(quintet, 2H, J=7.1 Hz, OCH₂CH₂CH₂CH₃), 2.87(dd, 1H, J+16.2, 8.8 Hz, CH₂CO₂Et), 3.14(dd, 1H, J=16.2, 4.0 Hz, CH₂CO₂Et), 4.20(quartet, 2H, J=7.1 Hz, OCH₂CH₃), 4.261(t, 2H, J=6.7 Hz, OCH₂CH₂CH₂CH₃) 4.63(d, 1H, J=5.9 Hz, OH), 5.99(ddd, 1H, J=8.7, 5.8, 4.2 Hz,ArCH(OH)R), 6.691(d, 1H, J=15.9 Hz, alkene), 7.838(d, 1H, J=16.0 Hz, alkene), 8.057(d, 1H, J=1.8 Hz, ArH), 8.270(d, 1H, J=1.6 Hz, ArH), 9.059(d, 1H, J=2.6 Hz, ArH), 9.617(d, 1H, J=2.6 Hz, ArH); IR 3500, 1720sh, 1710, 1640, 1605, 1530, 1370, 1350, 1330 cm⁻¹; anal calcd for C₂₁H₂₄N₂O₇: C, H, N.

EXAMPLE 8

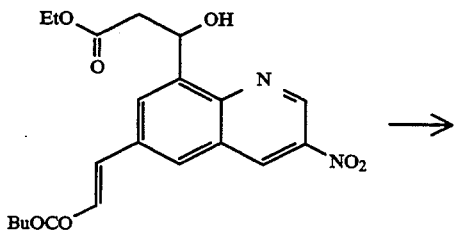

7

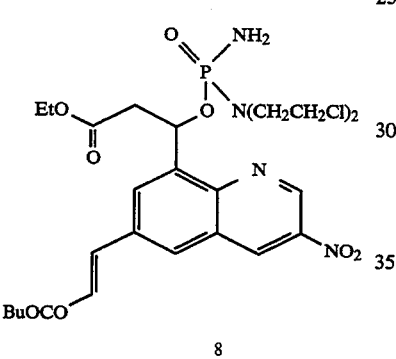

8

Preparation of N,N-bis(2-chloroethyl)—)ethyl 3-(6-[Z-(n-butyl propenoate)-3-yl)-3-nitroquinolin-8-yl) propanoate-3-yl)phosphoramide (8)

To a solution of 236 mg (0.57 mmol) of n-butyl-3-(8-[(ethyl 3-hydroxypropanoate)-3-yl]-3-nitroquinolin-6-yl) propenoate (7) in 5.5 ml of CH₂Cl₂ was added a solution of 192 mg (0.66 mmol) of thallous t-amyloxide (dissolved in 0.70 ml of fluorobenzene) in one portion. The mixture was stirred at room temperature under N₂ for 2 min., then a solution of 183 mg (0.71 mmol) of bis(2-chloroethyl) phosphoramidic dichloride in 1.0 ml of toluene was added. The resulting cloudy mixture was stirred for 10 min., and anhydrous ammonia was bubbled through the mixture for 2 min. After stirring for an additional 10 min., 3 ml of CHCl₃ and 20 ml of aqueous pH 7 buffer were added. The organic (lower) layer was separated, dried (MgSO₄), and filtered through a short column of Celite to remove the thallium salts. The crude products were purified by flash chromatography on 8.2 g of silica; eluting first with 80:19:1 CH₂Cl₂:EtOAc:EtOH (v:v:v), then with 5:4:1 CH₂Cl₂:EtOAc:EtOAH (v:v:v). The first elution brought down several faint yellow and brown bands, the second elution brought down a dark orange-brown band, which contained the product. Evaporation of solvents gave 238 mg (68%) of N,N-bis(2-chloroethyl)(ethyl 3-(6-[Z-(n-butyl propenoate)-3-yl]-3-nitroquinolin-8-yl)propanoate-3-yl)phosphoramide (8), a mixture of diastereomers, as a tan powder: ¹H NMR δ 0.98(t, 3H, J=7 Hz, CH₂CH₂CH₂CH₃), 1.220(t, minor isomer, J=7.3 Hz, OCH₂CH₃),1.287 (t, major isomer, J=6.8 Hz, OCH₂CH₃), 1.47 (sextet, 2H, J=7.4 Hz, CH₂CH₂CH₂CH₃), 1.72 (quintet, 2H, J=7.2 Hz, OCH₂CH₂CH₂CH₃), 2.87(dd, J=16.8, 10.0 Hz, major isomer, CH₂CO₂Et), 2.9–3.22 (m, both isomers, CH₂CO₂Et), 3.35–3.55(m, 4H, NCH₂CH₂Cl), 3.55–3.70(m, 6H, NCH₂C₂Cl and NH₂), 4.08–4.30(m, 4H, OCH₂R), 6.664(d, 1H, J=16.1 Hz, alkene), 6.84–6.95(m, 1H, ArCHORR'), 7,810(d, 1H, J=15.6 Hz, major isomer, alkene), 7.823(d, 1H, J=16.6 Hz, minor isomer, alkene), 8.044(bs, 1H, major isomer, ArH), 8.074(bs, 1H, minor isomer, ArH), 8.265(bs, 1H, minor isomer, ArH), 8.298(bs, 1H, major isomer, ArH), 9.037(m, 1H, both isomers), 9.605(d, 1H, J=2.9 Hz, major isomer, ArH), 9.629(d, 1H, J=2.9 Hz, ArH); ³¹P NMR δ−8.83 (major isomer), −9.70(minor isomer); anal calcd for C₂₅H₃₃N₄O₈Cl₂P: C, H, N.

EXAMPLE 9

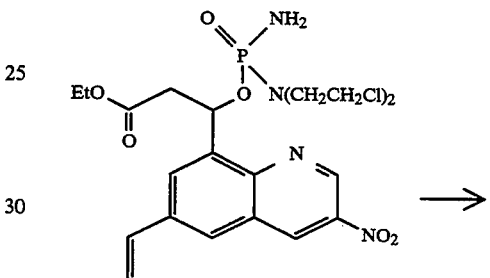

8

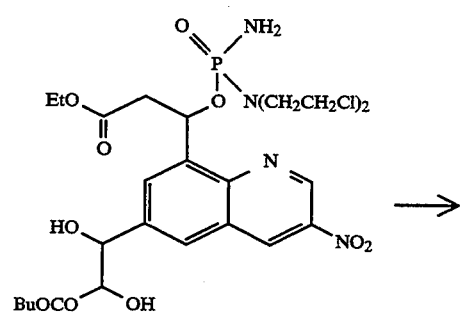

9

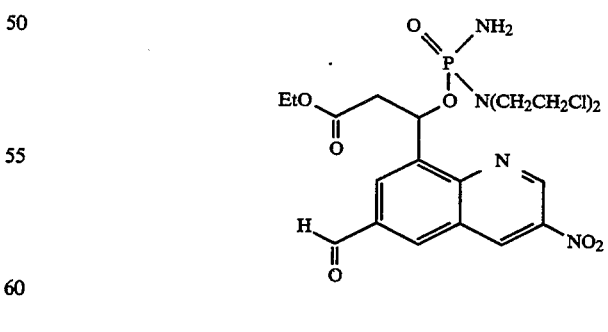

10

Preparation of N,N-bis (2-chloroethyl)-(ethyl 3-(3-nitroquinoline-6-carboxaldehyde-8-yl) propanoate-3-yl)phosphoramide (10)

To a stirred suspension of 4.85 g (7.83 mmol) of N,N-bis(2-chloroethyl)-ethyl 3-(6-[Z-(n-butylpropenoate)-3- yl)-3-nitroquinolin-8-yl)propanoate-3-yl)phosphoramide (8) in 100 ml of dioxane (distilled from SnCl₂) at room temp. was added 3.8 ml of OsO₄ (2.5 wt. % solution in t-butanol), the resulting brown mixture was stirred for 6 min. A solution of 9.0 ml (64 mmol) of dimethylaminoethyl acetate and 7.33 g (32.1 mmol) of periodic acid in 25 ml of water was then added in small portions as follows: a 4 ml portion to start, the remainder added slowly over a period of 30 min. After stirring for an additional 2 hr., the heterogeneous reaction mixture was poured into 500 ml of 5% aq. acetic acid, extracted with 2 portions of CHCl₃ (80 ml, 5 ml). The CHCl₃ extracts were washed with 500 ml of 5% aq. NaHCO₃, and 5 ml of 1-hexene and drying agent (Na₂SO₄) were added and the solution was allowed to stand for 30 min., filtered and the solvents evaporated to give 5.2 g of crude product. The crude product was purified by flash chromatography on 280 g of silica, eluting with 5:4:1 CH₂Cl₂:EtOAc:EtOH (v:v:v) to give 3.20 g (62%) of diol (9) as a mixture of diastereomers. This intermediate, a brown glass, was then oxidized further as follows.

To a rapidly stirred solution of 3.07 g (4.70 mmol) of 9 in 25 ml of dioxane (distilled from SnCl₂) and 6.3 ml of water at room temperature was added 2.03 g (9.49 mmol) of powdered NaIO₄ in small portions over a period of 10 min. After stirring for an additional 70 min., the reaction mixture was diluted with 300 ml of 1% aq. NaHCO₃, extracted with 2 portions of CHCl₃ (60 ml, 15 ml), the CHCl₃ extracts dried (Na₂SO₄) and the solvents removed in vacuo to give a crystalline crude product. The crude product was purified by flash chromatography on 190 g of silica, eluting with 5:4:1 CH₂Cl₂:EtOAc:EtOH giving 1.88 g (46%, based on olefin 8) of the major diastereomer of aldehyde N,N-bis (2-chloroethyl)-[ethyl 3-(3-nitroquinoline-6-carboxaldehyde-8-yl)propanoate-3-yl)propanoate-3yl)]phosphoramide (10) as an off-white crystalline solid, 0.152 g (3.7%) of the minor diastereomer of 10 as a glass, and one mixed fraction ( 0.154 g 3.7% ).

A small sample was recrystallized from toluene for elemental analysis: mp 157.5–159.5 C.(major isomer); ¹H NMR (major isomer) δ 1.2981t, 3H, J=7.3 Hz, CH₃), 2.86(dd, 1H, J=17.0, 10.0 Hz, CH₂CO₂Et), 3.17(dt, 1H, J=17.0, 2.7 Hz, CH₂CO₂Et), 3.41–3.60 (m, 6H, NCH₂CH₂Cl and NH₂), 3.60–3.70(m, 4H, NCH₂CH₂Cl), 4.238(quartet, 1H, J=7.1 Hz, OCH₃CH₃), 4.248(quartet, 1H, J=7.1 Hz, OCH₂CH₃), 6.905(td, 1H, J=9.5, 2.2 Hz, ArCHORR'), 8.504(d, 1H, J=1.8 Hz, ArH), 8.593(d, 1H, JH=1.8 Hz, ArH), 9.207(d, lit, J=2.7 Hz, ArH), 9.740(d, 1H, J=2.7 Hz, ArH), 10.238(s, 1H, ArCHO); ¹H NMR (minor isomer) 1.231(t, 3H, J=7.0 Hz, CH₃), 3.009(d, 2H, J=4.3 Hz, NH₂), 3.102(bd, 2H, J=6.7 Hz, CH₂CO₂Et), 3.38–3.52 (m, 4H,NCH₂CH₂Cl), 3.65 (t, 4H, J=7 Hz), 4.15 (quartet, 2H, J=7.4 Hz OCH₂CH₃), 6.92 (dt, 1H, J=8.7, 6.0 Hz, ArCHORR'), 8.523(d, 1H, J=1.8 Hz, ArH, 8.556(d, 1H, J=1.8 Hz, ArH), 9.213(d, 1H, J=2.7 Hz, ArH), 9.775(d, 1H, J=2.6 Hz, ArH), 10.254(s, 1H, ArCHO); ³¹P NMR (major isomer) δ −8,745; ³¹P NMR (minor isomer) δ −9.722; IR (major isomer) 3400, 3240, 1730, 1700, 1610, 1535, 1355, 1340 cm⁻¹.

EXAMPLE 10

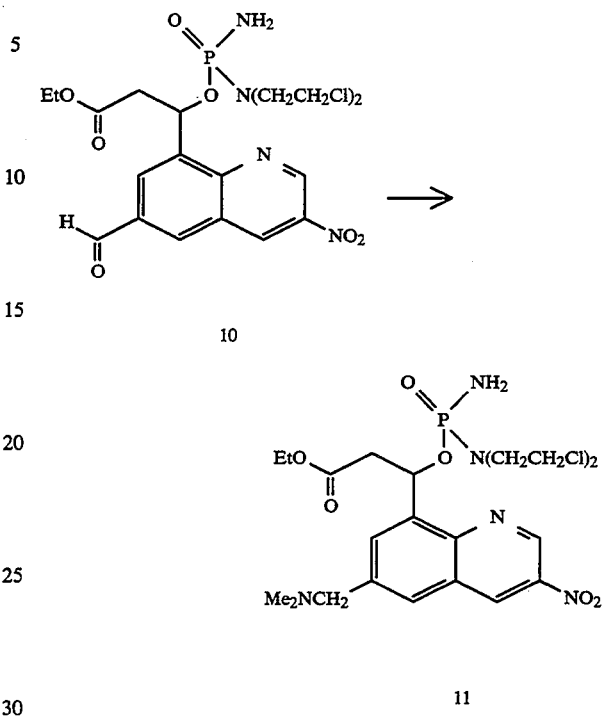

Preparation of N,N-bis (2-chloroethyl)-(ethyl 3-[6-(dimethylamino)methyl-3-nitroquinolin-8-yl]propanoate-3-yl) phosphordiamidate A suspension of 880 mg of powdered anhydrous CaSO₄, 340 Mg (4.2 mmol) of dimethylamine hydrochloride, and 0.80 ml of triethylamine in 1.5 ml CH₂Cl₂ was stirred for 10 min.; then 202 mg (0.39 mmol) of N,N-bis(2-chloroethyl)-[ethyl 3-(3-nitroquinoline-6-carboxaldehyde-8-yl) propanoate-3-yl] phosphoramide (10) (major isomer) and 194 mg (0.69 mmol) of tetra-n-butyl ammonium cyanoborohydride were added. The mixture was stirred for 25 min., filtered, and the insoluble solids washed with 25 ml of CHCl₃. The combined filtrate and washes were then placed on a column containing 5 g each of NaCl and CaBr₂.2H₂O (ground together with mortar and pestle). The column was eluted slowly with CHCl₃ to remove tetrabutylammonium salts: the eluate was discarded. The column contents were dissolved in 180 ml of 0.1M aq. NH₃, and the product extracted with 12 ml of CHCl₃ (4 portions) dried (CaSO₄), and the solvent evaporated to give 48 mg (22%) of N,N-bis (2-chloroethyl)-(ethyl 3-[6-(dimethylamino)methyl-3-nitroquinolin-8-yl)propanoate-3-yl]phosphordiamidate (11) as a light brown oil: ¹H NMR δ 1.278 (t, 3H, J=7.1 Hz, OCH₂CH₃), 2.312 (s, 6H, N(CH₃)₂), 2.93 (dd, 1H, J=17.8, 7.9 Hz, CH₂CO₂Et), 3.17 (dt, 1H, J=17.2, 2.6 Hz, CH₂CO₂Et), 3.35–3.50(m, 4H, NCH₂CH₂Cl), 3.56–3.69 (m, 8H, NCH₂CH₂Cl, NH₂, and ArCH₂N), 4.214 (quartet, 1H, J=7.1 Hz, OCH₂CH₃), 4.223 (quartet, 1H J=7.1 Hz, OCH₂CH₃), 6.872 (td, 1H, J=9.4,2.4 Hz, ArCHOOR'), 7.875 (s, 1H, ArH), 8.168 (s, 1H, ArH), 9.974 (d, 1H, J=2.6 Hz, ArH), 9.565 (d, 1H, J=2.6 Hz, ArH); ³¹P NMR δ −9.04; IR(neat) 3300bd, 2900, 2430, 1725, 1610, 1535, 1340 cm⁻¹.

EXAMPLE 11

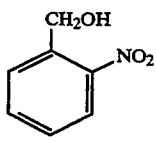

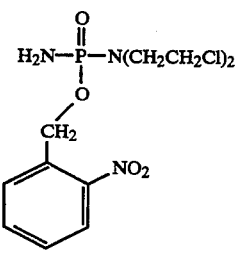

Preparation of 2-nitrobenzyl N,N-bis(2-chloroethyl) phosphorodiamidate

A solution of 2-nitrobenzyl alcohol (3.03 g, 19.8 mmol) in 125 ml of THF was placed under an atmosphere of nitrogen and cooled to 0°. A solution of n-butyl lithium (13 ml, 20.8 mmol) in hexanes was added dropwise. The resulting solution of alkoxide was added over 1 hour to a stirred solution of N,N-bis(2-chloroethyl)phosphoramidic dichloride (5.19 g, 20.0 mmol) in 250 ml of THF. After stirring at 0° for an additional hour, ammonia gas was bubbled through the reaction mixture. Stirring was continued for 1 hour at 0°, and the reaction mixture was filtered through a bed of diatomaceous earth and evaporated to dryness in vacuo. The crude product was purified by flash chromatography on silica gel (ethyl acetate, then methanol) to give 1.8 g (26%) of product as a pale yellow oil.

EXAMPLE 12

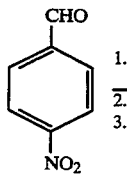

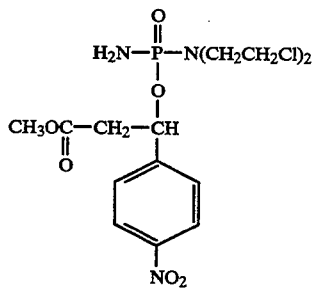

Preparation of methyl 3-(4-nitrophenyl)-3-(N,N-bis-(2-chloroethyl)phosphorodiamido) propionate A solution of lithium bis(trimethylsilyl)amide (20 ml of 1M, 20 mmol) was cooled to −78°, methyl acetate (1.5 g, 20 mmol) was added, and the resulting solution was stirred for 15 minutes. 4-Nitrobenzaldehyde (3.0 g, 20 mmol) was dissolved in a minimum volume of THF, and the resulting solution was added and stirred for an additional 15 minutes. The resulting alkoxide solution was added to a solution of N,N-bis(2-chloroethyl)phosphoramidic dichloride (10.4 g, 40 mmol) in 100 ml of THF at −40°. When the addition was complete, stirring was continued for an additional 15 minutes, and the mixture was allowed to warm to 0°. Ammonia gas was bubbled through the solution for 15 minutes, and the resulting mixture was purified by flash chromatography on silica gel (ethyl acetate) to give 3.0 g (35%) of product as an oil.

Similarly, using the procedures described herein and the appropriate starting materials the following compounds can also be prepared:

methyl 3-(2-nitrophenyl)-3-(N,N-bis(2-chloroethyl) phosphorodiamido)propionate.

methyl 3-(4-nitrophenyl)-3-(N,N,N,N tetrakis-(2-chloroethyl)phosphordiamido)propionate.

EXAMPLE 13

$$\text{alkyl-O-CO-CH}_3 + \text{CHO-R-(R}_5)_n-X_{n1} \longrightarrow$$

$$\underset{A}{\text{alkyl-O-CO-CH(OH)-R-(R}_5)_n-X_{n1}}$$

General procedure for the synthesis of 3-hydroxypropionate esters (A above)

The corresponding acetate ester (20.4 mmol) was added to a 1M solution of lithium bis-trimethylsilylamide (20.4 mmol, 1 equiv) in tetrahydrofuran at −78° and stirred for 15 min. Chlorotitanium triisopropoxide (21.4 mmol, 1.05 equiv) was added dropwise to the solution, and the reaction was stirred for 30 min at −78°. The nitroarylaldehyde (19.4 mmol, 0.95 equiv) was dissolved in a minimum volume of dry tetrahydrofuran and added all at once. The reaction was warmed to 0° and stirred for 30 min. The reaction was quenched with 10% HCl (100 mL). In the case of ethyl esters the resulting mixture was extracted with ethyl acetate (3×100 mL). For diethylaminoalkyl esters, the mixture was brought to pH 10 with aqueous potassium carbonate, filtered, and extracted with methylene chloride (3×100 mL). The organic extracts were dried (MgSO4), treated with activated carbon, filtered through a short column of silica gel, and evaporated. The resulting alcohols were used without further purification in the procedures below.

$$\underset{A}{\text{alkyl-O-CO-CH}_2-\overset{\overset{\text{OH}}{|}}{\text{CH}}-\text{R-(R}_5)_n-X_{n1}} \longrightarrow$$

$$\underset{B}{\overset{\overset{\overset{O}{\|}}{R_1R_2N-P-N-(CH_2CH_2Cl)_2}}{\underset{\text{alkyl-O-CO-CH}_2-\overset{|}{\text{CH}}-\text{R-(R}_5)_n-X_{n1}}{|}}}$$

General procedure for the synthesis of O-(1-aryl-2-carbethoxyalkyl)-N,N,N′N′-tetrakis(2-chloroethyl) phosphoramides (i.e. Compounds 12, 15, 16 and 17 having the general formula of B above)

Phosphorus trichloride (11.4 mmol) was dissolved in 100 mL of dry methylene chloride. N,N-bis-(2-chloroethyl)-amine hydrochloride (24.0 mmol) was suspended in this solution. Triethylamine (60 mmol) was added dropwise with stirring, taking care to maintain the temperature below 30° C.; the resulting mixture was stirred for 15 min. The appropriate alkyl-3-aryl-3-hydroxypropionate (5.7 mmol) was dissolved in a minimum volume of dry methylene chloride and added all at once. The mixture was stirred for 30 min. The reaction was cooled to −20° C. and t-butyl hydroperoxide (12 mmol) was added as a 3.0M solution in 2,2,4-trimethylpentane. The reaction was maintained at −20° C. for 1 hour and allowed to warm to room temperature. The mixture was filtered, then washed with 10% aqueous HCl (1×100 mL) and water (2×100 mL). The methylene chloride solution was dried (MgSO4), filtered, and evaporated. The residue was subjected to flash chromatography on silica using 1:3 ethyl acetate:hexanes as the eluent.

General procedure for the synthesis of O-[1-aryl-2-(2-N,N-dimethylamino)alkoxycarbonyl]-N,N,N'N'-tetrakis(2-chloroethyl)phosphoramides (i.e. Compounds 13 and 14 having the general structure of B above)

These compounds were prepared as their hydrochlorides by an analogous route with the following modifications to the procedure. After all the reactants were added and the solution was warmed to room temperature, the mixture was filtered and washed with water (3×100 mL). The methylene chloride solution was tested with moist pH paper and made acidic if necessary with concentrated hydrochloric acid before drying and filtering. The residue was subjected to flash chromatography on silica using 1:2 methanol:ethyl acetate as the eluent.

Spectral Characterization of Compounds 12–18
O-(1-(4-nitrophenyl)-2-carbethoxyethyl)-N,N,N',N'-tetrakis(2-chloroethyl)phosphoramide (i.e. Compound 12)

¹H-NMR (CDCL3) δ 8.29 (d, 2H), 7.62 (d, 2H), 5.90 (q, 1H), 4.11 (q, 2H), 3.68 (m, 5H), 3.47 (m, 8H), 3.16 (m, 4H), 2.76 (dd, 1H), 1.22 (t, 3H).

³¹P-NMR (CDCl3) δ −8.53 (s).

O-(1-(4-nitrophenyl)-2-(2-N,N-dimethylaminoethoxycarbonyl)ethyl)-N,N,N'N'-tetrakis-(2-chloroethyl)-phosphoramide (i.e. Compound 13)

¹H-NMR (CDCl3) δ 8.27 (d, 2H), 7.80 (d, 2H), 6.32 (m, 1H), 4.61 (m, 1H), 4.39 (m, 1H), 3.68 (m, 6H), 3.42 (m, 8H), 3.15 (m, 6H), 2.92 (s, 6H).

³¹P-NMR (CDCl3)δ −8.67 (s).

O-(1-(4-nitrophenyl)ethyl)-N,N,N'N'-tetrakis-(2-chloroethyl)-phosphoramide (i.e. Compound 18)

¹H-NMR (CDCL3)δ 8.26 (d, 2H), 7.61 (d, 2H), 5.67 (q, 1H), 3.68 (m, 4H) 3.47 (m, 8H), 3.24 (m, 4H), 1.66 (d, 3H).

³¹P-NMR δ −8.42 (s).

O-(1-(5-nitro-2-thiophene)-2-(2-N,N-dimethylaminoethoxycarbonyl)ethyl)-N,N,N'N'-tetrakis-(2-chloroethyl)-phosphoramide (i.e. Compound 14)

¹H-NMR (CDCl3) δ 7.84 (d, 1H), 7.48 (d, 1H), 6.62 (q, 1H), 4.66 (m, 1H), 4.41 (m, 1H), 3.67 (t, 4H), 3.49 (m, 8H), 3.35 (m, 7H), 3.14 (dd, 1H), 2.96 (s, 6H).

³¹P-NMR δ −8.43 (s).

O-(1-(5-nitro-2-thiophene)-2-carbethoxyethyl)-N,N,N'N'-tetrakis(2-chloroethyl)phosphoramide (i.e. Compound 15)

¹H-NMR δ 7.83 (d, 1H), 7.14 (d, 1H), 6.06 (q, 1H), 4.16 (q, 2H), 3.66 (m, 6H), 3.53 (m, 3H), 3.38 (m, 5H), 3.20 (m, 3H), 2.93 (dd, 1H), 1.27 (t, 3H).

³¹H-NMR δ −8.30 (s).

O-(1(6-methyl-5-nitro-2-pyridyl)-2-carbethoxyethyl)-N,N,N'N'-tetrakis(2-chloroethyl)phosphoramide (i.e. Compound 16)

¹-NMR δ 8.30 (d, 1H), 7.51 (d, 1H), 5.82 (q, 1H), 4.10 (q, 2H), 3.64 (m, 6H), 3.55 (m, 3H), 3.43 (m, 6H), 3.28 (m, 2H), 3.02 (dd, 1H), 2.82 (s, 3H), 1.22 (t, 3H).

³¹P-NMR δ −8.32 (s).

O-(1-(4-nitro-2-pyridyl)-2-carbethoxyethyl)-N,N,N',N'-tetrakis(2-Chloroethyl)phosphoramide (i.e. Compound 17)

¹H-NMR (CDCl3) δ 8.91 (d, 1H), 8.20 (dd, 1H), 8.14 (dd, 1H), 5.93 (dd, 1H), 4.15 (Q, 2H), 3.69 (m, 5H), 3.54 (m, 8H), 3.39 (m, 5H), 1.47 (t, 3H).

³¹P-NMR (CDCL3) δ −8.46.

EXAMPLE 14

Preferred Species

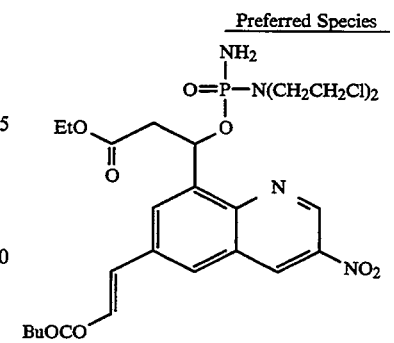

8

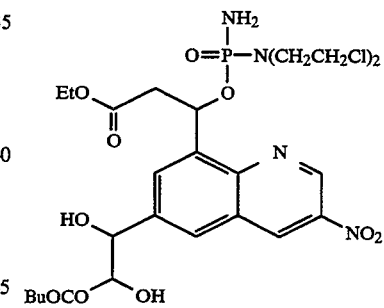

9

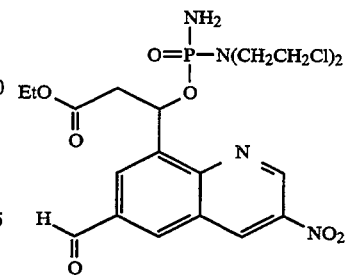

10

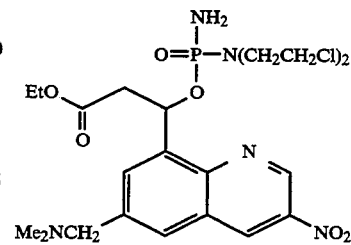

11

-continued
Preferred Species

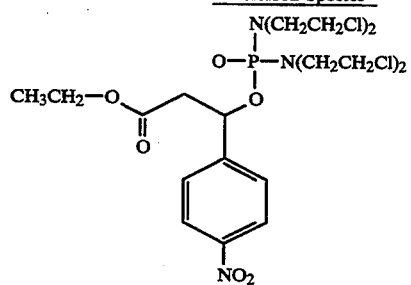 12

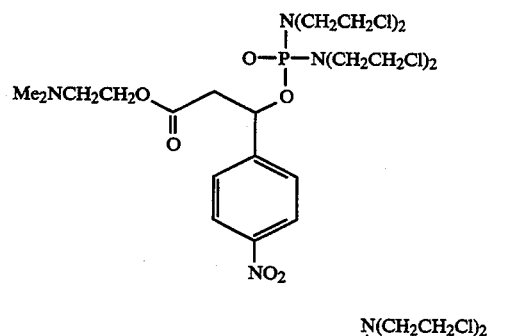 13

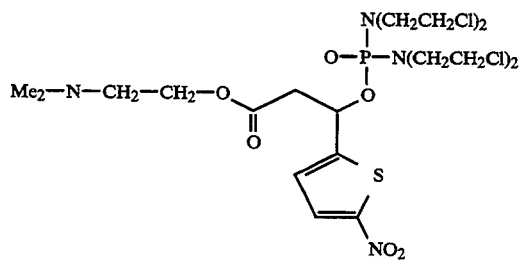 14

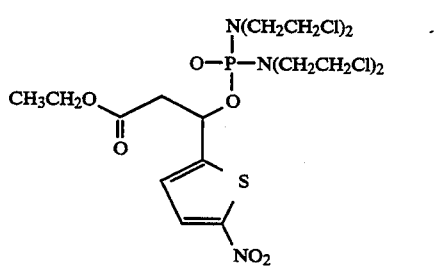 15

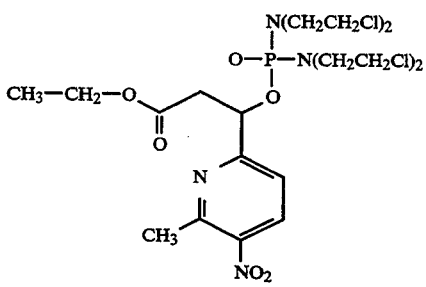 16

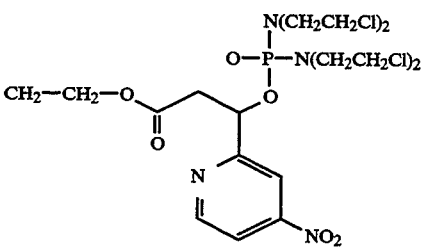 17

-continued
Preferred Species

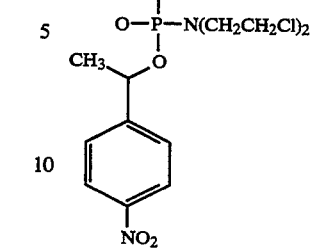 18

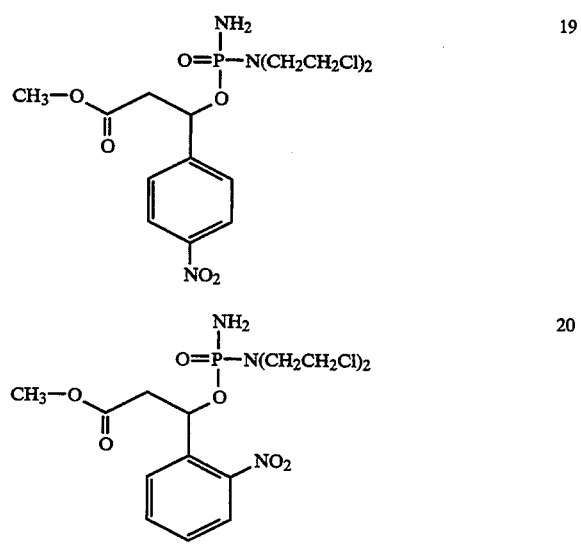

EXAMPLE 15

Cytoxicity of Compounds Under Aerobic and Hypoxic Conditions

The In Vitro cytotoxic activity of representative compounds under hypoxic and aerobic conditions were evaluated as follows.

A soft agar colony-forming assay according to the procedure of Chu and Fischer, *Biochem. Pharmacol.*, 17, 753–767 (1968) was used and modified where necessary. Cultured mouse L1210 and P388 sensitive cells were purchased from EG&G Mason Research Institute, Tumor Bank, Worchester, Ma. Cultured cyclophosphamide resistant L1210 and P388 cells were obtained from Dr. Robert Struck of Southern Research Institute, Birmingham, Ala. Typically, the desired cells ($2-3 \times 10^6$ cells/ml) in exponential growth and suspended in 6.5 ml of Fischer's medium (Gibco Lab., Grand Island, N.Y.) were divided into six groups (1 control and 5 treated groups) containing an equal number of cells in 1 ml. These cells were then treated with varying doses of drug diluted with media to give a total volume of 10 ml, and incubated for one hour at 37° C. The cells were washed three times with 3 ml of supplemented Fischer's medium (containing 10% horse serum) by centrifuge ($800 \times g$), removal of media by suction, and resuspension of the pellet in media (5 ml). A 1-ml portion was used to determine the cell count with a Coulter counter. From the remainder, a 5-ml suspension of cells was prepared at a density of $10^5$ cells/ml, and between $10^2$ and $10^5$ cells were placed on soft agar and incubated at 37° C. Colonies were counted after 10 days. The log of the surviving fraction was plotted vs. drug concentration and from this plot the $LC_{99}$ was obtained. (By definition, the $LC_{99}$ value represents the concentration of drug necessary to effect a 99% cell kill.)

The results of this test on representative compounds of the present invention is depicted in Table 1.

Protocols For Evaluation of Hypoxic Cell Selectivity Using KHT/iv Cells

KHT/iv cells were adapted to cell culture from tile mouse KHT sarcoma by Dietmar Siemann, University of Rochester. Cells were maintained in Eagle's basal medium and 10% fetal calf serum for all experiments. Cells in exponential growth were trypsinized from monolayer cultures and separated from one another by agitation in a gas-tight syringe at a density of $1-2 \times 10^7$ cells/ml for 15 minutes at 37°. The cells were then resuspended in HEPES-buffered Eagle's medium contained in stirred gas-tight vials at a final density of $2 \times 10^7$ cells/ml; before cells or drugs were added, the vials were pre-equilibrated with humidified gas having tile composition 95:5 air:$CO_2$ for aerobic treatment or 95:5 nitrogen:$CO_2$ from hypoxic treatment. Oxygen tension in the hypoxic medium was approximately 100 ppm after tile equilibration period. Drug was dissolved a volume of ethanol that would give a final ethanol concentration of 1% in the medium; this concentration of ethanol had no effect on the plating efficiency of control cell preparations. Cells were incubated with drug under aerobic or hypoxic conditions at 37° for 4 hours. The cells were then removed from the vials, washed with drug-free medium, counted, and plated for cell survival using a standard clonogenic assay. Cell surviving fraction was plotted vs. drug concentration, and the $LC_{99}$ values were obtained from the least squares equation.

The results of this test on representative compounds of the present invention is depicted in Table 2.

Protocol for Evaluation of Cytoxicity Against B16 Melanoma Cells

B16 melanoma cells in exponential growth ($2-3 \times 10^6$ cells in 10 ml of serum-free MEM medium) were treated with drug for 2 hr. The cells were separated, washed, and resuspended in MEM medium supplemented with 10% fetal bovine serum. The cells were plated in 60-mm culture dishes at a density of 50-50,000 cells/plate (depending upon the drug concentration used) and then incubated for 8 days in a $CO_2$ incubator at 37°. The colonies were fixed and stained with 0.5% crystal violet in ethanol and counted. The log of the surviving fraction was plotted against drug concentration, and from this plot the concentration required to reduce the colony number to 10% of control ($LC_{90}$) was determined.

The results of this test on representative compounds of the present invention are tabulated in Table 3.

Protocol for Evaluation of Aerobic and Hypoxic Selectivity Against Human Colon Cancer HT29 Cells HT29 human colon cancer cells were maintained in exponential growth in α-MEM medium supplemented with 10% fetal bovine serum and 25 mM HEPES buffer, and cultured at 37° C. and 3% $CO_2$. For drug treatments, $1-2 \times 10^6$ cells in 10 ml of medium were transferred to glass reaction vials. For the hypoxic experiments, the medium was first gassed for 3 hr with 95% nitrogen/5% $CO_2$ to achieve a partial pressure of oxygen <100 ppm. These cell suspensions were then treated with drug at different concentrations under either aerobic or hypoxic conditions for 4 hr in the reaction vials. The medium was removed, the cells were washed, and a colony formation assay was carried out as described above in Example 15. Colonies with less than 50 cells were counted 12-14 days after plating. The log of the surviving fraction was plotted against drug concentration, and from this plot the concentration required to reduce the colony number to 10% of control ($LC_{90}$) was determined. The results of this test on representative compounds of the present invention are depicted in Table 4.

TABLE 1

In vitro cytotoxic evaluation of compounds against cyclophosphamide sensitive (/O) and resistant (/CP) L1210 and P388 Murine Leukemia Cells

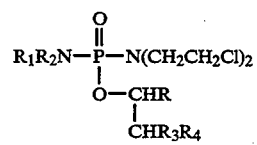

| | | | LC99 | | | |
|---|---|---|---|---|---|---|
| | | | L1210 | | P388 | |
| R | R1, R2, R4 | R3 | /O | /CP | /O | /CP |
| Ph | H | COOCH3 | 350 | ND | 300 | ND |
| 2-NO2Ph | H | COOCH3 | 172 | ND | 134 | ND |
| 4-NO2Ph | H | COOCH3 | 138 | 152 | 82 | 77 |

*ND means not done

TABLE 2

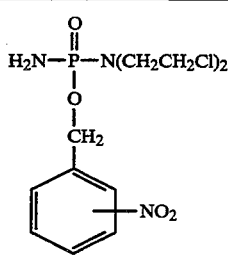

LC99 (μM) vs. KHT Sarcoma

| Compound | Aerobic | Hypoxic |
|---|---|---|
| 2-nitro | 700 | 230 |
| 4-nitro | 320 | 120 |

TABLE 3

Drug Concentration (μM) required to kill 90% of Clonogenic Tumor Cells In Vitro

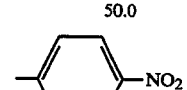

| Cpd # | R—(R$_5$)$_n$—X$_{n1}$[a] | alkyl/alkylamine | B/16[b] | HT29[c] Aerobic | HT29[c] Hypoxic |
|---|---|---|---|---|---|
| 12 | 1 | CH$_2$CH$_3$ | >100 | 80 | 12 |
| 13 | 1 | CH$_2$CH$_2$NMe$_2$ | <2 | 60 | 35 |
| 14 | 2 | CH$_2$CH$_2$NMe$_2$ | 2.8 | 7.5 | 3.0 |
| 15 | 2 | CH$_2$CH$_3$ | 3.0 | | |
| 16 | 3 | CH$_2$CH$_3$ | 150 | 110 | 25 |
| 17 | 4 | CH$_2$CH$_3$ | 50.0 | 80 | 35 |

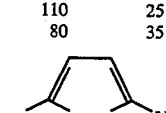

[a]Numbers correspond to structures at lower right
[b]Mouse melanoma cell line
[c]Human colon tumor cell line

TABLE 4

Drug Concentration (μM) required to kill 90% of Clonogenic Tumor Cells In Vitro

| | HT29[a] Aerobic | HT29[a] Hypoxic |
|---|---|---|
| 18 | >500 | 45 |
| 11 | 700 | 95 |

[a]Human colon tumor cell line

Comments on Aerobic vs. Hypoxic Cell Data

In this assay, smaller values for the LC$_{99}$ or LC$_{90}$ correspond to the more potent drug and/or conditions, because equivalent (99% or 90%, respectively) cell kill requires less drug. Thus selectivity for tumor cell killing under oxygen deficient conditions has been demonstrated.

As shown by the data compounds of the present invention exhibit a selectivity factor of at least three in KHT sarcoma and adenocarcinoma cell lines. In other words, compounds of the present invention are at least three times more toxic to these tumor lines under hypoxic conditions than to identical cells under normal oxic conditions. Thus, selectivity for tumor cell killing under oxygen deficient conditions has been demonstrated.

The above preferred embodiments and examples are given to illustrate the scope and spirit of the present invention. These embodiments and examples will make apparent to those skilled in the art other embodiments and examples. Such other embodiments are examples within the contemplation of the present invention. Therefore the present invention should be limited only by the appended claims.

What is claimed is:

1. A compound of the formula:

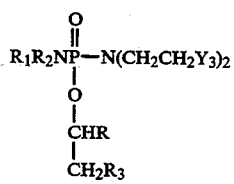

wherein R$_1$ and R$_2$ are individually H, CH$_2$CH$_2$Y$_3$, CH$_2$CH$_2$OCH$_3$, CH$_2$CH$_2$OH or R$_1$ and R$_2$ taken together with the nitrogen to which they are attached, form a morpholino ring, Y$_3$ halo, R$_3$ is H, lower(alkoxy)carbonyl or dialkylamino lower alkyleneoxycarbonyl and R is nitrophenyl, nitrothienyl, nitropyridyl, nitropyrrolyl, nitroquinolyl or nitro-N-loweralkylimidazolyl; or a pharmaceutically acceptable salt thereof.

2. The compound of claim 1 wherein $R_1=R_2$ and $R_1$ and $R_2$ are H, $CH_2CH_2Cl$, or $CH_2CH_2Br$.

3. The compound of claim 1 wherein $R_3$ is carbomethoxy, carboethoxy or $-COOCH_2CH_2N(CH_3)_2$.

4. The compound of claim 1 wherein R is 2-nitrophenyl, 4-nitrophenyl, 4-nitro-2-pyridyl, 5-nitro-2-pyridyl, 2-nitroquinolyl, 3-nitroquinolyl, 4-nitroquinolyl,

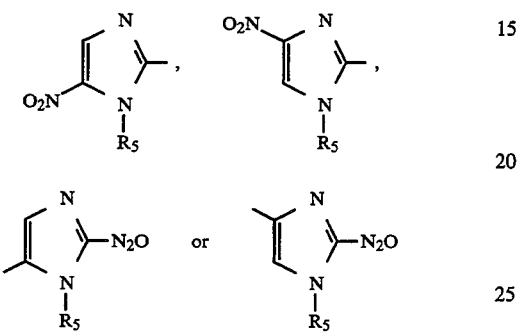

wherein $R_5$ is lower alkyl.

5. The compound according to claim 1 which is 2-nitrobenzyl-N,N-bis(2-chloroethyl)phosphorodiamidate, methyl 3-(4-nitrophenyl)- 3-(N,N-bis-(2-chloroethyl) phosphormido)propionate, methyl 3-(2-nitrophenyl)-3-(N,N-bis(2 -chloroethyl)phosphoramido)propionate, methyl 3-(4-nitrophenyl)-3-(N,N,N'N'-tetrakis(2-chloroethyl) phosphoroamido)propionate, N,N-bis(2-chloroethyl)-(ethyl 3-[6-(dimethylamino)methyl-3-nitroquinolin-8-yl]propanoate-3-yl) phosphordiamidate, or 0-[1-thiophene-2-(2-N,N-dimethylamino)carbonyl]-N,N,N',N'-tetrakis(2-carbethoxyethyl)-N,N,N',N-tetrakis(2-chloroethyl)phosphorodiamidate.

6. The compound of claim 1 having the formula:

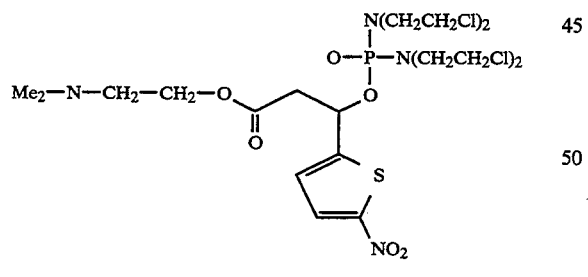

or

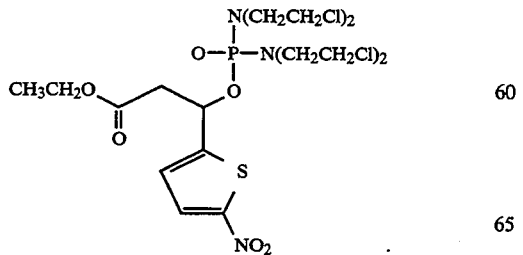

7. The compound of claim 1 having the formula:

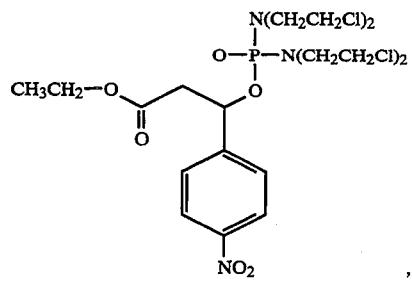

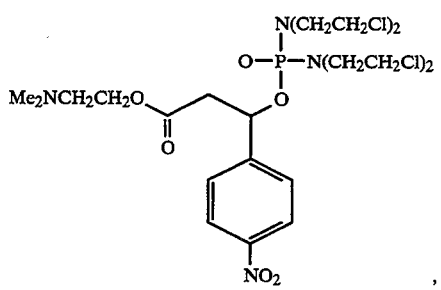

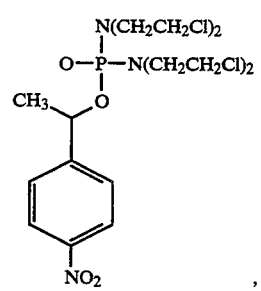

8. A compound of the formula:

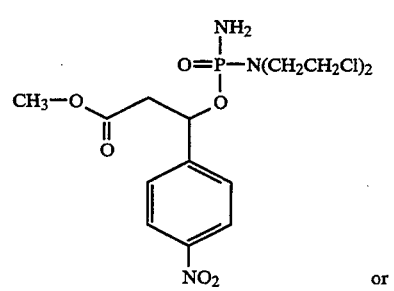

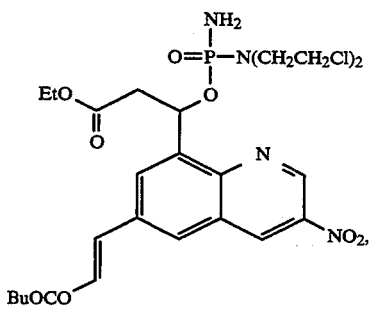
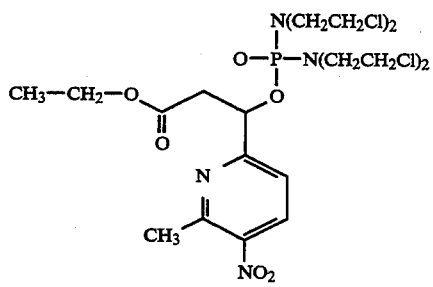
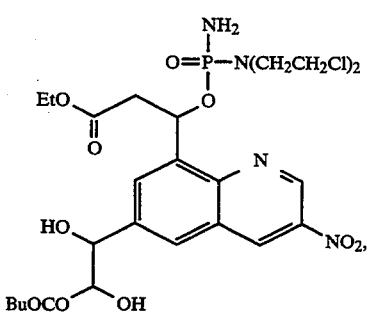
or
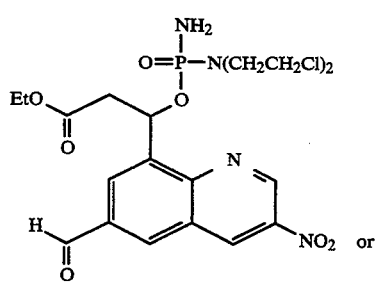
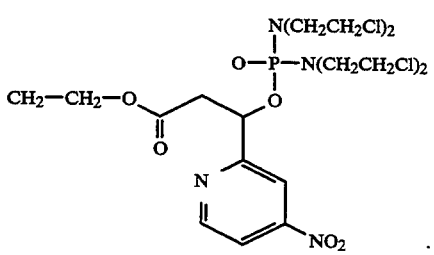
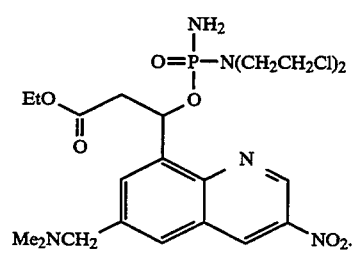
9. A compound of the formula:
* * * * *

UNITED STATES PATENT AND TRADEMARK OFFICE
CERTIFICATE OF CORRECTION

PATENT NO. : 5,403,932

DATED : April 4, 1995

INVENTOR(S) : Borch et al.

Page 1 of 2

It is certified that error appears in the above-indentified patent and that said Letters Patent is hereby corrected as shown below:

Column 5 Line 42 "s-position" should read --α-position-- therefor.

Column 16 Line 44 "propenoate" should read --propenoate (7)-- therefor.

Column 17 Line 61 ":EtOAH" should read --:EtOH-- therefor.

Column 19 Line 40 "hyde-8-yl)propanoate-3-yl)propanoate-3yl" should read --hyde-8-yl)propanoate-3yl-- therefor.

Column 19 Line 46 "1.2981t," should read --1.298(t,-- therefor.

Column 19 Line 55 "lit" should read --1H-- therefor.

Column 19 Line 65 "-8,745" should read -- -8.745 -- therefor.

Column 23 Line 68 "$^{31}$H-NMR" should read --$^{31}$P-NMR-- therefor.

UNITED STATES PATENT AND TRADEMARK OFFICE
CERTIFICATE OF CORRECTION

PATENT NO. : 5,403,932
DATED : April 4, 1995
INVENTOR(S) : Borch et al.

It is certified that error appears in the above-indentified patent and that said Letters Patent is hereby corrected as shown below:

Column 24 Line 5 "$^1$-NMR" should read --$^1$H-NMR-- therefor.

Signed and Sealed this

Seventeenth Day of September, 1996

Attest:

BRUCE LEHMAN

Attesting Officer  Commissioner of Patents and Trademarks